US012622602B2

(12) United States Patent
Armstrong

(10) Patent No.: US 12,622,602 B2
(45) Date of Patent: May 12, 2026

(54) MEASUREMENT DEVICE

(71) Applicant: Sony Interactive Entertainment Inc.,
Tokyo (JP)

(72) Inventor: Calum Armstrong, London (GB)

(73) Assignee: Sony Interactive Entertainment Inc.,
Tokyo (JP)

( * ) Notice: Subject to any disclaimer, the term of this
patent is extended or adjusted under 35
U.S.C. 154(b) by 830 days.

(21) Appl. No.: 17/968,276

(22) Filed: Oct. 18, 2022

(65) Prior Publication Data

US 2023/0134249 A1 May 4, 2023

(30) Foreign Application Priority Data

Nov. 3, 2021 (GB) ...................................... 2115787

(51) Int. Cl.
*A61B 5/107* (2006.01)

(52) U.S. Cl.
CPC ........ *A61B 5/1072* (2013.01); *A61B 2562/02*
(2013.01)

(58) Field of Classification Search
CPC ..... A61B 5/1072; A61B 5/1077; A61B 5/107;
A61B 2562/02; G01B 5/02; G01B 5/025;
G01B 5/08; A61C 19/04; G02C 13/005;
A41H 1/02
See application file for complete search history.

(56) References Cited

U.S. PATENT DOCUMENTS

| | | | | |
|---|---|---|---|---|
| 2,752,689 A | * | 7/1956 | Adams ................... | A61C 19/00 |
| | | | | 33/513 |
| 4,823,476 A | * | 4/1989 | Curtin ..................... | A41H 1/02 |
| | | | | 33/1 K |
| 6,132,045 A | | 10/2000 | Gauvreau | |
| 8,276,288 B1 | | 10/2012 | Yu | |
| 11,033,204 B2 | * | 6/2021 | Massonneau .......... | G06F 3/013 |
| 2005/0150124 A1 | | 7/2005 | Greenawalt et al. | |
| 2006/0075648 A1 | * | 4/2006 | Madsen ................ | G01B 5/207 |
| | | | | 600/587 |

(Continued)

FOREIGN PATENT DOCUMENTS

| | | |
|---|---|---|
| CN | 207182864 U | 4/2018 |
| CN | 211432923 U | 9/2020 |

(Continued)

OTHER PUBLICATIONS

Examination Report for corresponding Application No. GB 2115787.
0, 3 pages dated Mar. 22, 2024.

(Continued)

*Primary Examiner* — Devin B Henson
(74) *Attorney, Agent, or Firm* — Kilpatrick Townsend &
Stockton LLP

(57) ABSTRACT

An anthropometric measurement device for measuring ana-
tomical features includes: a sheet having a width and a
length; a plurality of incisions extending from an edge of the
sheet, each of the plurality of incisions spaced apart a
distance so as to define a plurality of slats between the
incisions. The slats are configured to be displaced in a
direction normal to the plane of the sheet and held in
position when the edge of the sheet is pressed over the
anatomical feature, so as to indicate a dimension of the
feature.

20 Claims, 3 Drawing Sheets

(56)                    References Cited

U.S. PATENT DOCUMENTS

2017/0360330 A1    12/2017  Shifflett
2021/0307647 A1*   10/2021  Kahn  ................... A61B 5/1072

FOREIGN PATENT DOCUMENTS

WO        2019094114  A1    5/2019
WO        2021194487  A1    9/2021

OTHER PUBLICATIONS

EP22201377.3 , "Communicaiton Pursuant to Article 94(3) EPC",
Dec. 2, 2024, 4 pages.
Extended European Search Report for corresponding Application
No. EP 22201377.3, 7 pages dated Mar. 3, 2023.
Search Report for corresponding Application No. GB2115787.0, 4
pages dated Apr. 6, 2022.

\* cited by examiner

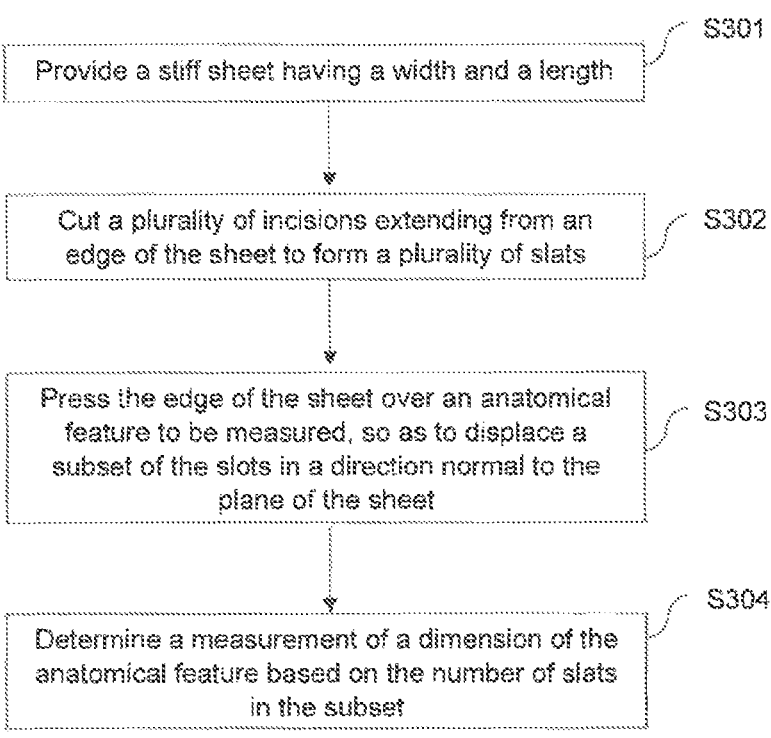

Provide a stiff sheet having a width and a length — S301

Cut a plurality of incisions extending from an edge of the sheet to form a plurality of slats — S302

Press the edge of the sheet over an anatomical feature to be measured, so as to displace a subset of the slots in a direction normal to the plane of the sheet — S303

Determine a measurement of a dimension of the anatomical feature based on the number of slats in the subset — S304

FIGURE 3

MEASUREMENT DEVICE

The present invention relates to devices and methods for measuring anthropometric features, and in particular devices and methods for measuring head dimensions.

BACKGROUND

Improvements in media technologies have allowed audio, visual and interactive content to be tailored for each consumer of the media. In order to provide such tailored user experiences, it has become increasingly desirable to obtain measurements of user's anatomy such as the head and ears to personalise content delivered to each user. For example, obtaining head-related transfer functions (HRTFs) of users enables delivery of improved audio experiences. Generation and utilisation of personalised HRTFs require the measurement of certain anthropometric features of the user, such as head dimension.

Taking physical measurements of a user has traditionally been done with tools such as callipers but this is not always possible to do in a simple or remote manner. The user must have access to suitable equipment (e.g. pair of callipers), which is often not the case, and even when in possession of such equipment, assistance by a second person is usually required as the user cannot easily measure his own head. Furthermore, such physical measurements are prone to errors in alignment and calibration. For example, when taking head measurements using a pair of callipers, which can only measure the distance between two exact points in space, it is often difficult to ensure that they are placed symmetrically about the widest point of the head routinely across measurements for multiple different users.

Attempts have been made to implement digital techniques utilising cameras and smart phone applications, machine learning models, computer vision and the like, but these tools are still also prone to error and are not available to everyone without the required equipment and computation.

There is, therefore, a need for a simple and robust technique for accurately measuring anthropometric features of a user, which is easy to implement and which is accessible by a wide audience.

The present invention seeks to mitigate at least some of the above problems.

SUMMARY OF THE INVENTION

According to an aspect of the disclosure, there is provided a measurement device for measuring anatomical features, the device comprising: a sheet having a width and a length; a plurality of incisions extending from an edge of the sheet, each of the plurality of incisions spaced apart a distance so as to define a plurality of slats between the incisions, wherein the slats are configured to be displaced in a direction normal to the plane of the sheet and held in position when the edge of the sheet is pressed over the anatomical feature, so as to indicate a dimension of the feature.

By having a sheet with cantilevered slats on an edge, a user can perform anthropometric measurements of their own anatomical features with ease and accuracy. For example, when measuring head width, a user can place the board over his head and sweep across in a given direction, such that the head displaces a number of slats depending on how wide it is. The number of slats which have been displaced may be counted to provide an indication of the head width. The slats may all have a uniform width, in which case the exact measurement of the head width can be obtained by multiplying the number of slats with the width of the slats—with a measurement error being the width of each slat. A significant advantage of the devices disclosed herein is that it is almost guaranteed that the 'widest point' of the head (or other anthropometric feature) is being measured each time, which is otherwise tricky with prior art devices such as callipers.

The sheet may comprise a scale which runs along the direction of the dimension being measured. The scale may run perpendicular and adjacent to the plurality of incisions.

The subset of slats which are displaced by contact with the user's anatomy under measurement may be configured to be easily distinguished from the slats which have not been displaced. The displaced slats may preferably be held in position once displaced from the plane of the sheet, in which the non-displaced slats remain. Preferably, the material of the sheet is selected to provide sufficient stiffness such that when a slat is displaced by a force having component normal to its plane, the maximum displacement is maintained even after application of the force. In other words, when the edge containing the slats is pressed over a user's anatomy (e.g. head) to displace a subset of the slats, the subset may remain displaced in place even after the sheet is moved away from the anatomy being measured.

In other examples, a uni-directional lock mechanism may be implemented to ensure that the displaced slats remain in position at or near the maximum displacement once pushed by contact with the user's anatomy. The sheet may comprise a latch configured to interact with a displaced slat to hold it into place.

In other examples, the device may comprise other means for indicating the slats which have been displaced by contact with the user. For example, the hinge region (e.g., the proximal end of a slat where the slat adjoins the rest of the sheet and about which the slat is able to rotate with respect to the sheet) of each slat may be provided with an indicator. The indicator may comprise a colour changing substance which indicates that the slat has been engaged and displaced. The friction caused by the displacement of the slat about the hinge may be accompanied by generation of heat which could be used to trigger a change in colour of the colour changing substance.

Preferably the sheet may comprise a paper material such as paper or cardboard. In such a case, the stiffness may be affected by the thickness and basis weight of the paper or cardboard. Preferably, the paper or cardboard may have a basis weight of between about 150 gsm to about 450 gsm. More preferably, the paper or cardboard may have a basis weight of between about 200 to about 300 gsm. Such a range provides a good balance between ease of use (i.e., less initial force required to displace the slats) and reliability of measurements (i.e., the displaced subset of slats are easily distinguished from the non-displaced slats).

In some examples, the sheet may comprise plastics materials such as polyvinyl chloride (PVC), and/or acrylic based materials (e.g., acrylonitrile butadiene styrene ABS).

In some examples, one or more of the slats may further comprise one or more sub-incisions. The one or more sub-incisions may be of a second length different than the length of the incisions which define the slats. For example, one slat of 10 mm width may be formed from two incisions cut 10 cm into the sheet. That individual slat may be cut in half 5 cm into the sheet to form two sub-slats of 5 mm width and 5 cm length within the slat of 10 mm width. This may result in multiple levels of accuracy—push the sheet deeply over the object and its measurement can be taken with 10 mm precision; cover the object with a shallower depth and the measurement can be taken with 5 mm precision. This principle may be applied to provide multiple levels of sub-slats to provide multiple levels of accuracies.

In some examples, the device may comprise features to assist the user to align the device over the anatomical feature being measured. For example, the device may be provided with a visual marker to indicate where the sheet should be aligned when pressing the device over the feature. In some examples, an opening may be provided on the sheet, the opening configured to be complementary to a particular feature—e.g., nose or ear, when measuring head dimensions—such that the user can align the device over that feature. The opening may be located anywhere on the sheet, but preferably the opening may be positioned at the slats. The plurality of incisions may comprise a first set of incisions and a second set of incisions, and the first and second set may be spaced apart or separated by an opening. The number of slats in the first set and in the second set may be the same, causing the device to be symmetrical about the opening. In other examples, the first set of slats may have a greater or fewer number of slats than in the second set of slats.

The opening may be shaped and configured to fit over the user's ear. This may be useful when the device is configured to measure the depth of the user's head; the device may be aligned by slotting the opening over one ear. Once slotted, the user may then press the sheet against his head to displace a number of the slats.

The opening may also, or alternatively, be shaped and configured to fit over the user's nose. This may be useful when the device is configured to measure the width of the user's head; the device may be aligned by slotting the opening over the nose. Once slotted, the user may then press the sheet against his head to displace a number of the slats.

The depth of the opening (i.e., the dimension of the opening in the direction of the axis of the incisions) may be configured so as to provide measurement at a particular region of the head (or other anatomy). The dimension of the opening in the direction of measurement—the separation between the first and second set of slats—may be referred to as the width of the opening. Preferably, the opening is shaped and configured to position, in use, the device over the user's head so as to measure the head's dimensions at ear pinnae level. The opening may comprise one or more notches arranged to guide the height at which the measurement is taken. The device may comprise multiple such openings, providing for example a mixture of openings each configured for fitment over different features (e.g., one opening configured to slot over the user's nose, another opening configured to slot over the user's ear). Where the device comprises such an opening, it may be advantageous to individually measure each distance away from the opening. For example, where the device is configured for anthropometric measurements of the head, and an opening is included for alignment at the ear of the user's head, the depth of the head in front and behind the ear may be measured. This may allow the determination of more information about where the ear is positioned on the user's head. As such, when the device has been used and passed over the user's head to deflect the slats, the number of slats on each side of the opening may be counted to provide positioning and symmetry information about the user's head, and particularly of the orientation and position of the anatomical feature around which the opening has been aligned.

Some, or all of the slats may be spaced apart by a gap to prevent adjacent slats from exerting friction against each other. This may be achieved by having some or all of the incisions extend a given width. In other words, at least one of the plurality of incisions may laterally extend a second distance, such that slats adjacent to the at least one incisions may be spaced apart by the second distance. The spacing between each slat may ensure that each slat can more smoothly be displaced when in use, with less force required for the displacement.

The device may be used manually, meaning that the displaced subset of slats may be identified and counted by the user to determine the anatomical dimensions. In other examples, the process may be semi- or fully automated. For example, a camera may be used to detect the slats which have been displaced by contact with the user's anatomy under measurement. In some examples, the slats may be provided with markers at the tip (e.g., the distal ends of the slats, at the edge of the sheet) which facilitate recognition via the camera. The markers may be coloured, or provided with a pattern, for improved visibility. In some examples, a system comprising a camera and a processor can be used to monitor a live video feed, and configured to detect a displacement of a subset of the slats, and further configured to determine the anatomical dimensions based on the detected displacement of slats on the device.

The device may further comprise a central control circuit and a plurality of sensors. The plurality of sensors and central control circuit may be configured to detect displacement of the slats in the direction normal to the plane of the sheet and determine a measurement of the anatomical feature based on the detected displacement. Such an arrangement may allow the device to be electronically enabled so that measurements can be taken digitally and without the need for manual counting. This also allows the slat width to be reduced to improve precision, even to widths where manual counting would be impractical. Where sensors and control circuitry is used, the slats may not need to remain held in place once displaced. That is, the slats may be flexible such that they return to their natural position (i.e., in the same plane as the rest of the sheet) once measurement is completed. Where the device comprises the circuit and sensors, the sheet may preferably comprise a flexible material having an elasticity such that the slats are biased to return to the plane of the sheet when displaced. For example the sheet may comprise a plastic material such as PVC. This may allow the device to be used many times improving durability.

The plurality of sensors may comprise flex sensors located at each slat, each flex sensor configured to detect deflection of the respective slat. The detection may be a binary detection, where a discrete detection signal is sent when deflection of a slat (i.e., displacement out of the plane of the sheet) exceeds a pre-determined threshold. Alternatively, or in combination, the detection may be continuous or variable such that the detection signal is of variable intensity within a range, the intensity corresponding to the extent of deflection of each slat. Such an arrangement may be used to map out the three-dimensional shape of the anatomical feature under measurement. Similarly, the sensors may detect the deflection gradient (i.e., how quickly each slat gets deflected) as the device is passed over the anatomical feature. The detected deflection and related information such as deflection gradient may be passed to the control circuitry as deflection data. The sensors and circuitry may then be configured to generate an estimation of the three dimensional shape of the anatomical feature based on the deflection data from the sensors. The flex sensors may comprise sensor elements positioned at or near the hinge region of each slat. In other words, the sensor elements may extend across the regions adjoining each slat to the rest of the sheet. The control circuit may pass a current to each sensor element and the resistance of each sensor element may be varied by the bend across each element. The control circuit may comprise a communication interface, allowing the device to send output data derived from the deflection data to external devices. Based on the deflection data, the control circuity may further be configured to select an HRTF profile from a plurality of pre-determined HRTF profiles. The selected HRTF profile may be output to an external device.

The control circuit may process the obtained measurement and calculate features such as interaural level differences (ILD) and/or an interaural time difference (ITD), corresponding to level and time differences between the signals that reach either ear. Estimating the dimensions of the head, for example, may directly aid in estimating time of flight differences between the two each for either HRTF selection or personalisation.

The device may comprise a level indicator, configured to provide an indication of the orientation of the device. The level indicator may guide the user to orient the tool horizontally so that consistent measurements can be taken at a flat level. The device may also be provided with level sensors, to ensure that the device is flat for a standard width and/or depth measurement. The sensors may also simply detect the orientation of the device so that the angle at which the measurement is taken may be recorded. In some examples, the sensors may be configured to indicate to the user (e.g., by a notable sound such as a beep, or by visual cues such as a light indicator or screen) that a desired orientation has been achieved. In some examples, the desired orientation may be horizontal—e.g., about 0 degrees with respect to the ground surface. In some examples the desired orientation may be 45 degrees with respect to the ground surface, for example to provide measurement of the angular depth of a head. The desired orientation may be programmable for example on a control circuitry.

Although some select example methods and use of the devices described herein have been explained with respect to measurement of dimensions of a user's head, it will be appreciated that the same or similar principles may be applied for measuring other anatomies and anthropometric features. That is to say, mention of specific dimensions of the head in the disclosure may be replaced by other anatomical or anthropometric features unless explicit reference is made to head-specific features.

Whilst in the examples above the slats have been described as being formed by a plurality of incisions in a sheet material, similar principles may be applied in a device having slats connected to a frame by other means.

According to another aspect of the present disclosure, there is also provided an anthropometric measurement device for measuring anatomical features, the device comprising: a frame; a plurality of slats extending from the frame, each of the plurality of slats spaced apart a distance, wherein the slats are configured to be displaced in a direction normal to the plane of the frame and held in position when the plurality of slats is pressed over the anatomical feature, so as to indicate a dimension of the feature.

Each of the slats may comprise rod-like protrusions, extending from the frame. The frame may comprise a handle such that the user can hold the device by the frame. As such the device may take a comb- or brush-like form.

It will be appreciated that any one or more of the features described above with respect to the first aspect of the disclosure may be adapted and applied to the second aspect.

According to another aspect of the present disclosure, there is also provided a method of measuring anthropometric features, the method comprising the steps of: providing a sheet having a width and a length, cutting a plurality of incisions extending from an edge of the sheet, each of the incisions spaced apart a distance so as to define a plurality of slats between the incisions; pressing the edge of the sheet over the anthropometric feature, so as to displace a subset of the slots in a direction normal to the plane of the sheet; determining a measurement of a dimension of the feature by counting the number of slots in the subset.

Using the methods described herein, a user can take a simple piece of suitable sheet material, apply a plurality of similarly sized incisions to an edge of the sheet to create slats in the sheet, press the slatted edge of the sheet over the anatomy under measurement to displace a subset of the slats and determine a measurement of the anatomy in dependence on the number of slats in the subset.

It will be appreciated that any one or combination of the features described with respect to each aspect of the disclosure may be adapted and/or applied to another of the aspects described herein, with their associated effects and advantages.

BRIEF DESCRIPTION OF THE DRAWINGS

The invention will now be described by way of examples with reference to the accompanying drawings, in which:

FIG. 3 schematically illustrates an example method of measuring anthropometric features.

DESCRIPTION

An aspect of the present disclosure is a measurement device for measuring anthropometric features. An exemplary measurement device 1 is shown in an assembled and operational configuration in FIG. 1.

The example measurement device 1 comprises a sheet 2 having a plurality of incisions 3 along one edge, which define a series of slats 4 extending perpendicularly from the edge.

Figure 1:
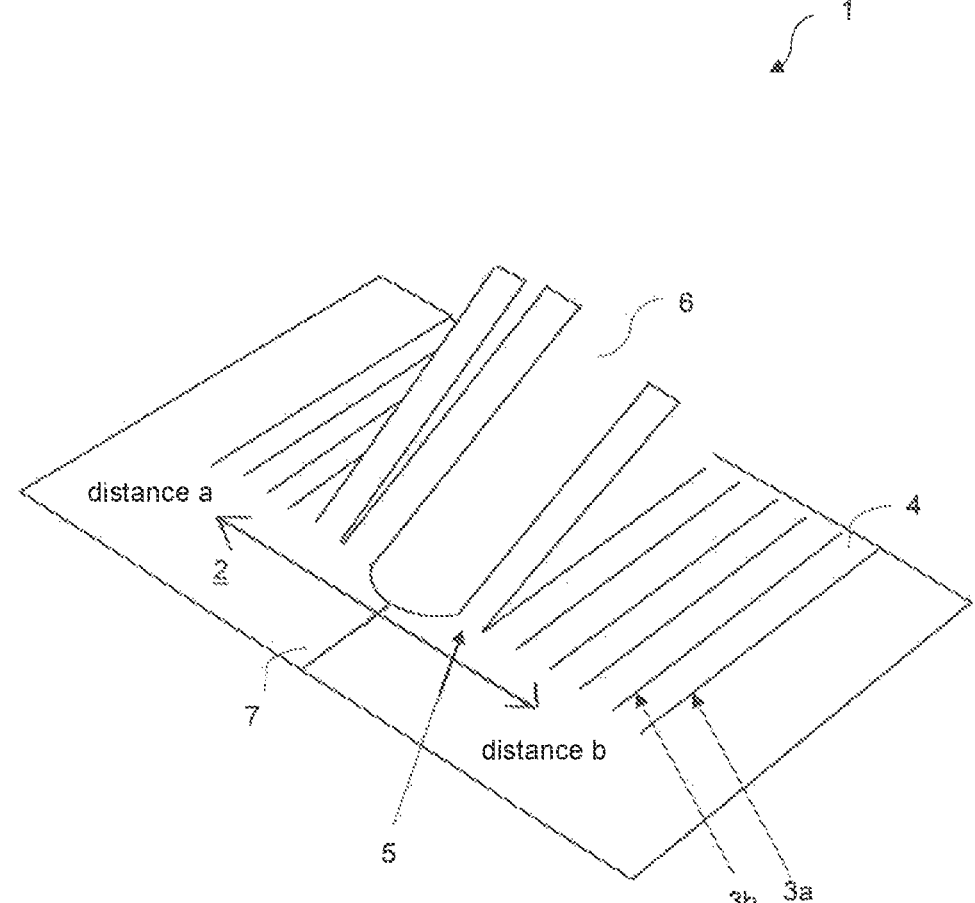
FIG. 1 schematically illustrates an example measurement device in an operational configuration.

In this example, the sheet is rectangular, having a length and a width, the length defining a longitudinal axis. The incisions 3 extend along the width axis, normal to the longitudinal axis, and to a length which extends over half of the sheet's width. The space on the sheet 2 between two consecutive incisions 3a, 3b defines a slat 4. The slat 4 can be thought of as a strip of sheet which is in connection to the rest of the sheet via a hinge 5. The hinge 5 is generally located at the proximal (or sheet-side, as opposed to the distal or edge-side) end points of the incisions 3a, 3b which define the slat 4. Each slat 4 is able to rotate out of the plane of the sheet about its respective hinge 5 as shown in FIG. 1 when a force is applied to a distal end of the slat 4. The slats 4 are generally independent meaning that the movement of one slat does not affect the position of the other slats.

The example device 1 of FIG. 1 further comprises an opening 6. The opening 6 is located at the edge of the sheet 2 having the incisions 3 so as to separate two sets of incisions 3 (and therefore two groups of slats 4). In this example, the opening 6 is positioned mid-way along the length of the sheet 2. A marker 7 is present on the sheet 2, the marker 7 indicating the exact midpoint along the length of the sheet 2. The opening 6 is configured for the user to align the device on the part of his body he is attempting to measure. For example, when measuring head dimensions, the user can align the device 1 using the opening 6 or marker 7 to centre the device 1 on his head. In some example devices, the opening 6 and/or marker 7 can be located at a different position for an off-centre alignment. In some example devices, the sheet 2 can comprise multiple openings 6 and/or markers 7.

In use, for example when measuring head dimensions, a user can take the device 1 and align it to the centre of his head by positioning the marker 7 or opening 6 over his nose, and press the edge of the sheet 2 against his head.

Figure 2A:
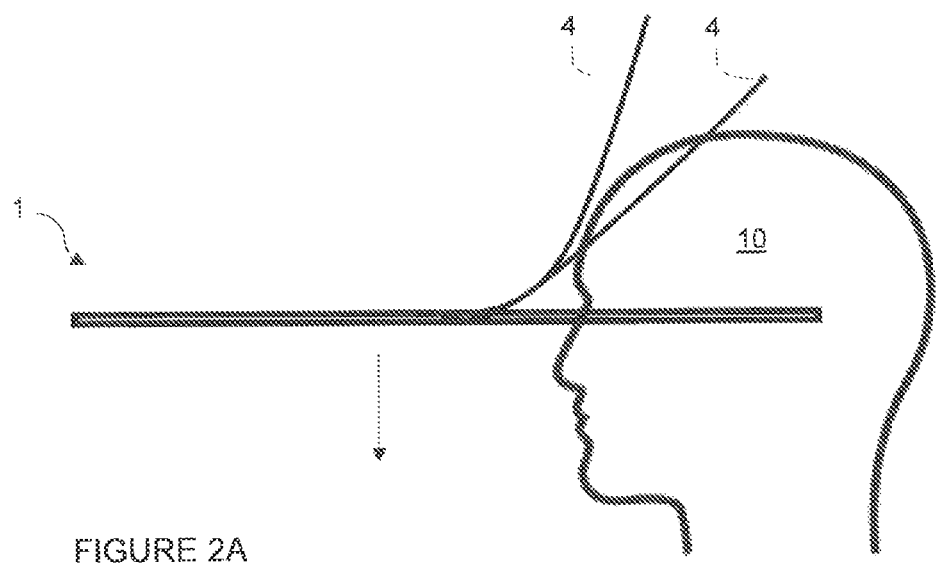
FIG. 2A schematically illustrates a cross sectional side view of an example measurement device in use.
Figure 2B:
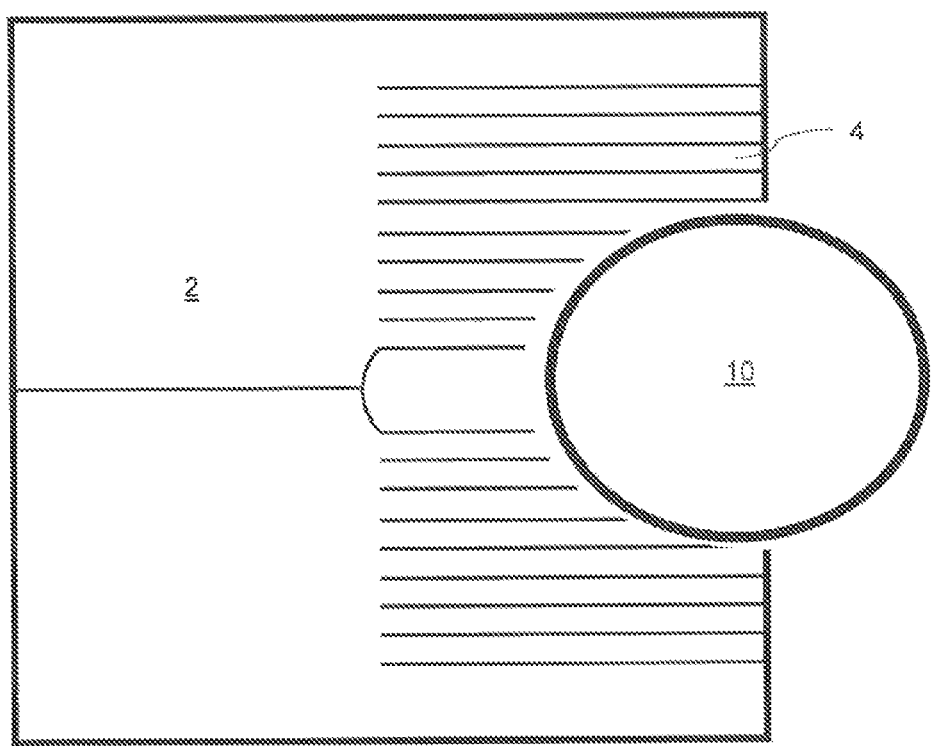
FIG. 2B schematically illustrates a cross sectional plan view of an example measurement device in use.

As shown in FIGS. 2A and 2B, the device 1 can be configured to measure a user's head dimensions. In the example use case, the device 1 is used to measure the width of a user's head 10. The device 1 is first held over the user's head at the region to be measured and, where the device 1 includes a marker 7 or an opening 6, an alignment is made to ensure the width will fit within the slatted region of the sheet 2. Then, the device 1 is actuated by movement—in the direction of the arrow—so as to press the edge containing the slats 4 against the relevant region of the head. The reactional force from the head 10 displaces a subset of the slats 4, which rotate about their respective hinges 5. Each of the slats may rotate to a different position depending on the shape of the head 10. The device can be moved until the full length of the head has passed through the device 1, or until a sufficient volume has been covered (e.g., until the widest point has been reached) and removed through a lateral motion. As noted above, once displaced about each hinge 5, the slats 4 remain in position. When the device 1 is removed from the head, the number of slats 4 which have been displaced can be counted and a resulting measurement for the width of the head can be derived. When each slat 4 is uniform in width, the number of displaced slats can be multiplied by the width to obtain the direct measurement, accurate to an error of one width.

The slat width may affect the ability of the hinge to hold the rotational position of the slat in place once displaced. Therefore, for a given material thickness or weight (e.g., gsm for paper), the width of each slat may be chosen to be as small as possible whilst still maintaining sufficient strength to retain its rotational position once displaced.

An aspect of the present disclosure is a method for measuring anatomical features. A flowchart of an exemplary method is shown in FIG. 3, wherein the method comprises the following steps:

Step 301: Provide a sheet having a width and a length.

As noted herein, the sheet can comprise any suitable material. The exemplary method will be described with respect to a cardboard sheet. Whilst the sheet can be of any suitable shape, a rectangular sheet is generally used, as it allows one long edge to be used as the measurement side to provide a larger range.

The sheet can be provided with incision markers to guide the incisions at the next step. The incisions markers can be printed onto the sheet at this step, or pre-provided with the sheet.

Step 302: Cut a plurality of incisions extending from an edge of the sheet to form a plurality of slats.

An edge of the sheet to be used for measurement is selected, and incisions are made to provide measurements. Where the sheet is not of regular dimensions—i.e., where all edges are not of the same length—typically the longest edge is selected for placement of the measurement components. In this example of a rectangular sheet, one of the two lengthwise edges is selected and incisions are made at the selected edge to form slats between the incisions. In other examples, slats can be located at multiple edges of the sheet.

The slats generated by the plurality of incisions at the edge of the sheet are to be used for measurement of the anatomical feature. The distance between adjacent incisions defines the width of each slat, and in turn the width of each slat defines the precision with which the measurement is made. In this example, the incisions at the edge of the sheet are spaced apart a uniform distance, resulting in slats of equal width. The distance between each incision can be selected according to the desired precision error. Preferably, the incisions are spaced apart a distance of 10 mm, as this provides a low measurement error whilst maintaining a wide enough slat that can support its weight when displaced.

In some examples, the slats are not all uniform in width. For example, incisions can be made at two different distances apart: a first distance and a second distance smaller than the first distance. This results in slats of at least two different widths, corresponding to at least two different measurement errors. The incisions can be made and configured such that some regions have a higher precision than others. For example, at the central region of the sheet (e.g., at the longitudinal midpoint of the sheet) where it is unlikely for the outer edges of the anatomy under measurement to be positioned, incisions can be made at the first, greater distance. At the regions of the sheet where the outer edges of the anatomy can be expected, incisions can be made at the second, smaller distance for the required precision. In one example, two incisions are made about the longitudinal midpoint of the sheet spaced apart a distance of 100 mm. A further ten incisions are made on either side of the initial two incisions, spaced apart a distance of 10 mm. The result is one large slat in the middle, where measurement is not expected, and smaller slats on either side where measurement precision is required. Where markers are provided on the sheet, the incisions are made following the markers on the sheet.

A larger incision can be made at this stage, to cut out an opening as described herein. The opening can be used for alignment, for example to align the sheet over the user's nose or ear when taking head measurements. In such cases the opening can be cut out to match the typical shape of a nose or ear. The opening can be cut out to align the sheet at a particular position or height on the user's head, in the manner disclosed herein. Alternatively, or in combination, a marker can be provided on the sheet for alignment.

Step 303: Press the edge of the sheet over an anatomical feature to be measured, so as to displace a subset of the slats in a direction normal to the plane of the sheet.

Specifically, the slats at the edge of the sheet are pressed over the anatomical feature to be measured, so as to displace some of the slats by reactional force. Where the sheet is provided with an opening or marker, the sheet is first aligned on the anatomical feature using the opening or marker. For example, where the opening is configured for slotting over the user's ear, the sheet is first positioned on the user's head so as to slot the ear into the opening.

Step 304: Determine a measurement of a dimension of the anatomical feature based on the number of slats in the subset.

The dimension of the anatomical feature can be determined for example by counting the number of slats that have been displaced in the previous step. Where the slats are all a uniform width, the actual measurement can be obtained by multiplying the number of displaced slats by the uniform width of the slats.

Embodiments of the present disclosure may be implemented in accordance with any one or more of the following numbered clauses:

1. A anthropometric measurement device for measuring anatomical features, the device comprising:
   a sheet having a width and a length;
   a plurality of incisions extending from an edge of the sheet, each of the plurality of incisions spaced apart a distance so as to define a plurality of slats between the incisions, wherein
   the slats are configured to be displaced in a direction normal to the plane of the sheet and held in position when the edge of the sheet is pressed over the anatomical feature, so as to indicate a dimension of the feature.

2. A measurement device according to clause 1, wherein the sheet comprises a scale running perpendicular and adjacent to the plurality of incisions.

3. A measurement device according to any of clauses 1 and 2, wherein the plurality of incisions comprises a first set of incisions and a second set of incisions, the first set and second set spaced apart a second distance by an opening.

4. A measurement device according to clause 3, wherein the sheet comprises a marker at the opening, the marker arranged, in use, to assist a user to centre the device over the user's head.

5. A measurement device according to any of clauses 3 and 4, wherein the opening is shaped to fit over the user's ear.

6. A measurement device according to any of clauses 3 and 4, wherein the opening comprises a groove to fit over the user's nose.

7. A measurement device according to any of clauses 3 to 6, wherein the opening comprises one or more notches, arranged to guide the height at which the measurement is taken.

8. A measurement device according to any of clauses 1 and 2, wherein at least one of the plurality of incisions has a second distance, such that slats adjacent to the at least one incision are spaced apart by the second distance.

9. A measurement device according to any preceding clause, further comprising:
   a central control circuit;
   a plurality of sensors, wherein the plurality of sensors and central control circuit are configured to detect displacement of the slats in the direction normal to the plane of the sheet and determine a measurement of the anatomical feature based on the detected displacement.

10. A measurement device according to clause 9, wherein the plurality of sensors comprises flex sensors located at each slat, each flex sensor configured to detect deflection of the respective slat.

11. A method of measuring anatomical features, the method comprising the steps of:
   providing a sheet having a width and a length,
   cutting a plurality of incisions extending from an edge of the sheet, each of the incisions spaced apart a distance so as to define a plurality of slats between the incisions;
   pressing the edge of the sheet over the anatomical feature, so as to displace a subset of the slots in a direction normal to the plane of the sheet;
   determining a measurement of a dimension of the feature based on the number of slats in the subset.

12. A method according to clause 11, wherein the edge of the sheet is pressed over a user's head, to measure a dimension of the user's head.

13. A method according to any of clauses 11 or 12, wherein the step of cutting a plurality of incisions comprises spacing each of the incisions apart a uniform distance, and the step of determining a measurement of a dimension of the feature comprises multiplying the number of displaced slats by the uniform distance of each slat.

The invention claimed is:

1. An anthropometric measurement device for measuring an anatomical feature, the anthropometric measurement device comprising:
   a sheet comprising a material and an edge;
   a plurality of incisions extending from the edge of the sheet, wherein adjacent incisions of the plurality of incisions are spaced apart from one another by one or more distances;
   a plurality of cantilevered slats located between the adjacent incisions of the plurality of incisions; and
   a plurality of hinges located at proximal ends of the plurality of cantilevered slats opposite the edge of the sheet, wherein:
      the plurality of hinges connects the plurality of cantilevered slats to the sheet,
      the material comprises a stiffness and elasticity defined by at least a thickness and basis weight of the sheet,
      the stiffness of the material is configured to allow the plurality of the hinges to open in a direction towards normal to a plane of the sheet rotating at least a subset of the plurality of cantilevered slats out of the plane of the sheet to a plurality of open positions, and
      the elasticity of the material is configured to maintain deformation of at least the subset of the plurality of cantilevered slats at the plurality of open positions.

2. The anthropometric measurement device of claim 1, wherein the sheet comprises a scale running perpendicular and adjacent to the plurality of incisions.

3. The anthropometric measurement device of claim 1, wherein the plurality of incisions comprises a first set of incisions and a second set of incisions, the first set of incisions and second set of incisions are spaced apart a first distance of the one or more distances and the first distance defines an opening in the sheet.

4. The anthropometric measurement device of claim 3, wherein the sheet comprises a marker at the opening, the marker arranged, in use, to assist a user to centre the anthropometric measurement device over the user's head.

5. The anthropometric measurement device of claim 3, wherein the opening is shaped to fit over a user's ear.

6. The anthropometric measurement device of claim 3, wherein the opening comprises a groove to fit over a user's nose.

7. The anthropometric measurement device of claim 3, wherein the opening comprises one or more notches, arranged to guide a height at which a measurement is taken.

8. The anthropometric measurement device of any of claim 1, wherein at least one pair of adjacent incisions of the plurality of incisions are spaced apart a first distance of the one or more distances and a remainder of adjacent incisions are spaced apart a second distance of the one or more distances.

9. The anthropometric measurement device of claim 1, further comprising: a central control circuit; and a plurality of sensors, wherein the plurality of sensors and central control circuit are configured to detect displacement of at least the subset of the plurality of cantilevered slats in the direction towards normal to the plane of the sheet and determine a measurement of the anatomical feature based on the detected displacement.

10. The anthropometric measurement device of claim 9, wherein the plurality of sensors comprises flex sensors located at each of the plurality of cantilevered slats, each flex sensor configured to detect deflection of the respective cantilevered slat.

11. The anthropometric measurement device of claim 1, wherein the material is a paper, cardboard, or plastics material.

12. The anthropometric measurement device of claim 11, wherein the material is the paper or the cardboard and the basis weight is between about 150 gsm to about 450 gsm.

13. A method of measuring an anatomical feature, the method comprising the steps of:

> providing a sheet comprising a material and an edge, wherein the material comprises a stiffness and elasticity defined by at least a thickness and basis weight of the sheet;
>
> cutting a plurality of incisions extending from an edge of the sheet, wherein adjacent incisions of the plurality of incisions are cut such that the adjacent incisions are spaced apart from one another by one or more distances that to define a plurality of cantilevered slats between the incisions and a plurality of hinges located at proximal ends of the plurality of cantilevered slats opposite the edge of the sheet and connects the plurality of cantilevered slats to the sheet;
>
> pressing the edge of the sheet over the anatomical feature, so as to displace a subset of the plurality of cantilevered slats in a direction towards normal to a plane of the sheet, wherein the stiffness of the material is configured to allow the plurality of hinges to open in the direction towards normal to the plane of the sheet rotating at least the subset of the plurality of cantilevered slats out of the plane of the sheet to a plurality of open positions, and the elasticity of the material is configured to maintain deformation of at least the subset of the plurality of cantilevered slats at the plurality of open positions; and
>
> determining a measurement of a dimension of the anatomical feature based on a number of slats in the subset of the plurality of cantilevered slats at the plurality of open positions.

14. The method of claim 13, wherein the anatomical feature is a user's head and the edge of the sheet is pressed over the user's head, to measure the dimension of the user's head.

15. The method of claim 13, wherein the one or more distances is a single uniform distance, and the step of determining the measurement of the dimension of the anatomical feature comprises multiplying the number of the slats in the subset of the plurality of cantilevered slats at the plurality of open positions by the uniform distance.

16. The method of claim 13, wherein the material is a paper, cardboard, or plastics material.

17. The method of claim 16, wherein the material is the paper or the cardboard and the basis weight is between about 150 gsm to about 450 gsm.

18. An anthropometric measurement device comprising:

> a sheet comprising a first edge, a second edge, a length, and a width, wherein the length defines a longitudinal axis of the sheet, the first edge defines the length of the sheet, the second edge defines the width of the sheet, and the first edge is perpendicular to the second edge;
>
> a plurality of incision markers extending from the first edge of the sheet, wherein adjacent incision markers of the plurality of incision markers are spaced apart from one another by one or more distances and wherein the plurality of incision markers extend: along a width axis that is normal to the longitudinal axis, and to a length which extends over half of the width of the sheet;
>
> a plurality of slats located between the adjacent incision markers of the plurality of incision markers; and
>
> a plurality of hinge regions located at proximal ends of the plurality of slats opposite the edge of the sheet, wherein the plurality of hinge regions connects the plurality of slats to the sheet.

19. The anthropometric measurement device of claim 18, further comprising an opening in the sheet defined by a pair of adjacent incision markers that are spaced apart from one another by a first distance of the one or more distances that is different from a remainder of the one or more distances, wherein the opening separates the plurality of incision markers into a first set of incision markers and a second set of incision markers, and wherein the opening extends: along the width axis that is normal to the longitudinal axis, and to a length which extends over half of the width of the sheet.

20. The anthropometric measurement device of claim 18, wherein each hinge of the plurality of hinges comprises a color changing substance.

\* \* \* \* \*